（12） United States Patent
Ponce et al.

(10) Patent No.: US 10,612,067 B2
(45) Date of Patent: Apr. 7, 2020

(54) METHODS AND APPARATUS FOR ASSAYS OF BACTERIAL SPORES

(71) Applicant: California Institute of Technology, Pasadena, CA (US)

(72) Inventors: Adrian Ponce, Los Angeles, CA (US); Gregory H. Bearman, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 120 days.

(21) Appl. No.: 15/666,512

(22) Filed: Aug. 1, 2017

(65) Prior Publication Data

US 2017/0342455 A1    Nov. 30, 2017

Related U.S. Application Data

(60) Division of application No. 13/437,899, filed on Apr. 2, 2012, now abandoned, which is a continuation of application No. 11/810,005, filed on Jun. 4, 2007, now Pat. No. 8,173,359, which is a continuation of application No. 10/355,462, filed on Jan. 31, 2003, now abandoned.

(60) Provisional application No. 60/414,170, filed on Sep. 27, 2002, provisional application No. 60/395,372, (Continued)

(51) Int. Cl.
| | |
|---|---|
| *C12Q 1/04* | (2006.01) |
| *G01N 33/543* | (2006.01) |
| *G01N 33/569* | (2006.01) |
| *G01N 33/84* | (2006.01) |
| *G01N 21/64* | (2006.01) |

(52) U.S. Cl.
CPC ......... *C12Q 1/04* (2013.01); *G01N 33/54306* (2013.01); *G01N 33/56911* (2013.01); *G01N 33/84* (2013.01); *G01N 21/6408* (2013.01)

(58) Field of Classification Search
CPC .... C12M 1/3466; C12M 23/08; C12M 41/14; G01N 35/025; G01N 35/00029
USPC .............................................. 435/287.36, 7.1
See application file for complete search history.

(56) References Cited

U.S. PATENT DOCUMENTS

| | | |
|---|---|---|
| 2,752,280 A | 6/1956 | Cooke et al. |
| 4,259,313 A | 3/1981 | Frank et al. |
| 4,587,223 A | 5/1986 | Erkki et al. |

(Continued)

FOREIGN PATENT DOCUMENTS

| | | |
|---|---|---|
| EP | 1478912 | 11/2004 |
| WO | WO 01/53525 A2 | 7/2001 |

OTHER PUBLICATIONS

Pikramenou, Z. et al. "Luminescence from Supramolecules Triggered by the Molecular Recognition of Substrates." Coordination Chemistry Reviews, vol. 132, pp. 181-194. 1994.

(Continued)

*Primary Examiner* — Michael L Hobbs
(74) *Attorney, Agent, or Firm* — Lewis Roca Rothgerber Christie LLP

(57) ABSTRACT

Described herein are methods and apparatus for assays of bacterial spores. In particular, methods and apparatus for lateral flow immunoassay for bacterial spore detection and quantification, live/dead assay for bacterial spores, lifetime-gated measurements of bacterial spores and imaging bacterial spores using an active pixel sensor, and unattended monitoring of bacterial spores in the air are described.

16 Claims, 10 Drawing Sheets

Related U.S. Application Data filed on Jul. 12, 2002, provisional application No. 60/353,268, filed on Feb. 1, 2002.

(56) References Cited

U.S. PATENT DOCUMENTS

| | | | |
|---|---|---|---|
| 6,599,715 B1 * | 7/2003 | Vanderberg | C12Q 1/04 435/242 |
| 6,787,104 B1 | 9/2004 | Mariella, Jr. | |
| 7,563,615 B2 | 7/2009 | Ponce et al. | |
| 8,173,359 B2 | 5/2012 | Ponce et al. | |
| 2002/0018203 A1 | 2/2002 | Battle et al. | |
| 2003/0064507 A1 * | 4/2003 | Gallagher | B01F 9/10 435/287.2 |
| 2003/0113230 A1 * | 6/2003 | Cordery | A47G 29/1207 422/68.1 |
| 2003/0135032 A1 * | 7/2003 | Lewis | C12N 15/52 536/23.1 |
| 2004/0141879 A1 | 7/2004 | Loomis et al. | |
| 2008/0113384 A1 | 5/2008 | Ponce et al. | |

OTHER PUBLICATIONS

Yu, J. et al. "Direct observation of intramolecular energy transfer from a beta-diketonate to terbium (III) ion encapsulated in a cryptand." Chemical Physics Letters, vol. 187 (3), pp. 263-268. Dec. 1991.
Alpha, B. et al. "Luminescence Probes: The $Eu^3$ and $Tb^3$— Cryptates of Polypyridine Macrobicylic Ligands." Angew. Chem. Int. Ed. Engl., vol. 26 (12), pp. 1266-1267. 1987.
Stein, G. and Wurzberg, E. "Energy gap law in the solvent isotope effect on radiationless transitions of rare earth ions." The Journal of Chemical Physics, vol. 62, 208, pp. 208-213. 1975.
Sorenson, W.G. "Fungal Spores: Hazardous to Health?" Environmental Health Perspectives, vol. 107, Supplement 3, pp. 469-472. Jun. 1999.
Roberts, T.A. and Hitchins, A.D. "Resistance of Spores." in Gould, G.W. and Hurst, A. (ed.) The Bacterial Spore. New York, Academic Press. Chapter 16, pp. 611-670. 1969.
Office of Space Science, National Aeronautics and Space Administration. Planetary Protection Provisions for Robotic Extraterrestrial Missions. Washington D.C. Effective Date: Apr. 20, 2011. 49 pgs.
National Aeronautics and Space Administration. "NASA standard procedures for the Microbiological Examination of Space Hardware, NHB 5340. ID." Jet Propulsion Laboratory Communication. 1980. 27 pgs.
Communication pursuant to Article 96(2) EPC issued for European Patent Application No. EP03707656.9 filed Jan. 31, 2003 in the name of California Institute of Technology. dated Jun. 12, 2007.
Notice of Allowance issued for U.S. Appl. No. 12/553,952, filed Sep. 3, 2009 in the name of Adrian Ponce et al. dated Apr. 13, 2015.
Final Office Action dated Jul. 25, 2007 for U.S. Appl. No. 10/987,202, filed Nov. 12, 2004 in the name of Adrian Ponce et al.
Examiner's Answer to Appeal Brief dated Jul. 31, 2013 for U.S. Appl. No. 11/453,296, filed Jun. 13, 2006 in the name of Adrian Ponce et al.
Setlow, P. "Resistance of Bacterial Spores." Bacterial Stress Responses. Ed. Storz, G. and Henngge-Aronis, G. Washington D.C. American Society for Microbiology. Chapter 14, pp. 217-230, 2000.
Ponce, A. "Lateral-flow immunoassay with DPA-triggered Tb luminescence," NASA Tech Briefs. vol. 27 (No. 3). pp. 6a-7a. 2003.
Rasband, W. S. Image J. U.S. National Institutes of Health, Bethesda, Maryland, U.S.A, Archived image of http://rsb.info.nih.Gov/ij/ from Nov. 27, 2005.
Non-Final Office Action issued for U.S. Appl. No. 10/987,202, filed Nov. 12, 2004 in the name of Adrian Ponce et al. dated Feb. 25, 2008.
Final Office Action issued for U.S. Appl. No. 11/453,296, filed Jun. 13, 2006 in the name of Adrian Ponce et al. dated May 1, 2012.
Non-Final Office Action issued for U.S. Appl. No. 12/533,938, filed Sep. 3, 2009 in the name of Adrian Ponce et al. dated Jan. 4, 2012.
Final Office Action issued for U.S. Appl. No. 12/533,938, filed Sep. 3, 2009 in the name of Adrian Ponce et al. dated Jan. 30, 2013.
Non-Final Office Action issued for U.S. Appl. No. 12/533,952, filed Sep. 3, 2009 in the name of Adrian Ponce et al. dated Jan. 4, 2012.
Final Office Action issued for U.S. Appl. No. 12/533,952, filed Sep. 3, 2009 in the name of Adrian Ponce et al. dated Feb. 13, 2013.
www.tetracore.com Retrieved on May 14, 2013.
www.skcwest.com Retrieved on May 14, 2013.
www.cem.com Retrieved May 14, 2013.
www.oceanoptics.com Retrieved on May 14, 2013.
Office of Space Science, National Aeronautics and Space Administration, Planetary Protection Provisions for Robotic Extraterrestrial Missions, vol. NPG 8020.12C. Washington, D.C., 1999 (from P127-USP2).
Bottiger, J.R. et al. "Aerosol Generation for Testing BW Detectors," First Joint Conference on Point Detection for Chemical and Biological Defense. Oct. 2000, pp. 294-308.
Supplementary European Search Report for EP 03707656 filed Jan. 31, 2003 in the name of California Insitute of Technology. dated Nov. 7, 2006.
Supplementary Partial European Search Report for EP 03707656 filed Jan. 31, 2003 in the name of California Insitute of Technology, dated Nov. 7, 2006 (.
EP Communication 97(2) issued for European Patent Application No. EP02806005.1 filed Nov. 27, 2002 in the name of California Institute of Technology, dated Jul. 26, 2007.
Supplementary EP Search Report issued for European Patent Application No. EP02806005.1 filed Nov. 27, 2002 in the name of California Institute of Technology, dated Nov. 15, 2004.
Kozuka, et al. "Ultrastructural localization of diplicolinic acid in dormant spores of bacillus subtillis by immunoelectron micrscopy with colloidal gold particles." Journal of Bacteriology, vol. 162 (No. 3), pp. 12501254. 1985.
Canada et al. "Binding of Terbium and Cisplatin to C13 Human Ovarian Cancer Cells using Time-Resolved Terbium Luminescence." Biochmica et Biophysics Acta, vol. 1448, pp. 85-98 (1998) Abstract Only.
Zaitoun et al. "Chelating Behavior Between Metal Ions and EDTA in Sol-Gel Matrix." Journal of Physical Chemistry B, vol. 101, pp. 1857-1860. 1997 Abstract Only.
Ponce, A. et al. "Bacterial endospore quantification using lanthanide dipicolinate luminescence" NASA Tech Briefs, vol. 26, p. 56. 2002.
Fox, K. et al. "Comparison of survivor curves of Bacillus subtilis spores subjected to wet and dry heat." Journal of Food Science, vol. 34, pp. 518-521. 1969.
Koike, J. et al. "Survivor rates of some terrestrial microorganisms under stimulated space conditions." Advances in Space Research, vol. 12 (No. 4), pp. 271-274. 1992.
Anonymous. "NASA standard procedures for the microbiological examination of space hardware, NHB 5340.1B." Jet Propulsion Laboratory Communication. 1980.
Husmark, U. et al. "The influence of hydrophobic electrostatic and morphological properties on the adhesion of Bacillus spores." Biofouling, vol. 5, pp. 335-344. 1992.
Weicek, K. et al. "Adhesion of Bacillus spores to inanimate materials: effects of substratum and spore hydrophobicity." *Biofouling*, vol. 3, pp. 139-149. 1991.
Zottola, E.A. "Characterization of the attachment matrix of Pseudomonas fragi attached to non-porous surfaces." *Biofouling*, vol. 5, pp. 37-55. 1991.
Venkateswaran, K. et al. "Molecular microbial diversity of a spacecraft assembly facility." Systematic and Applied Microbiology, vol. 24 (No. 2), pp. 311-320. 2001.

\* cited by examiner

DPA  Tb³⁺

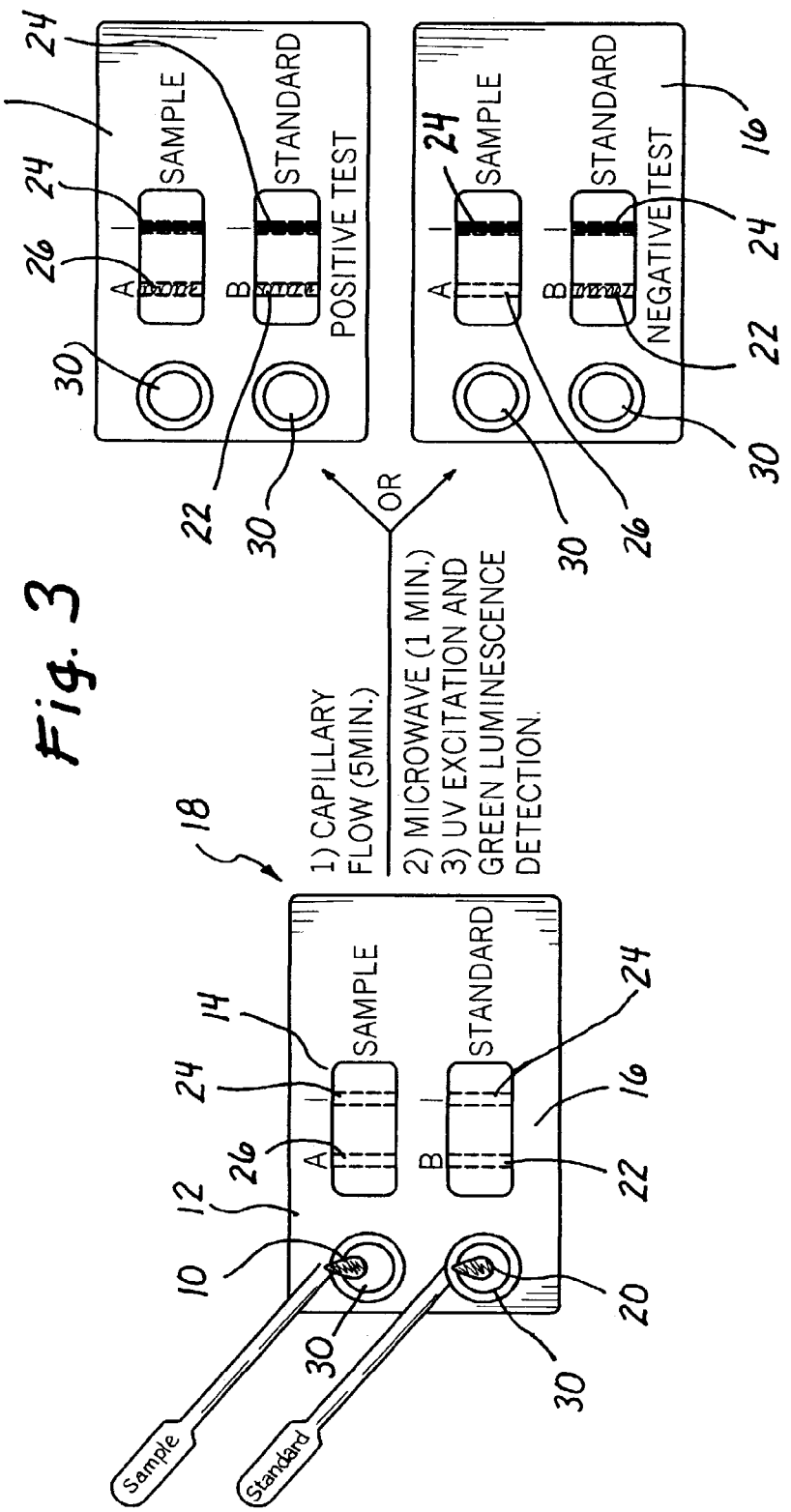

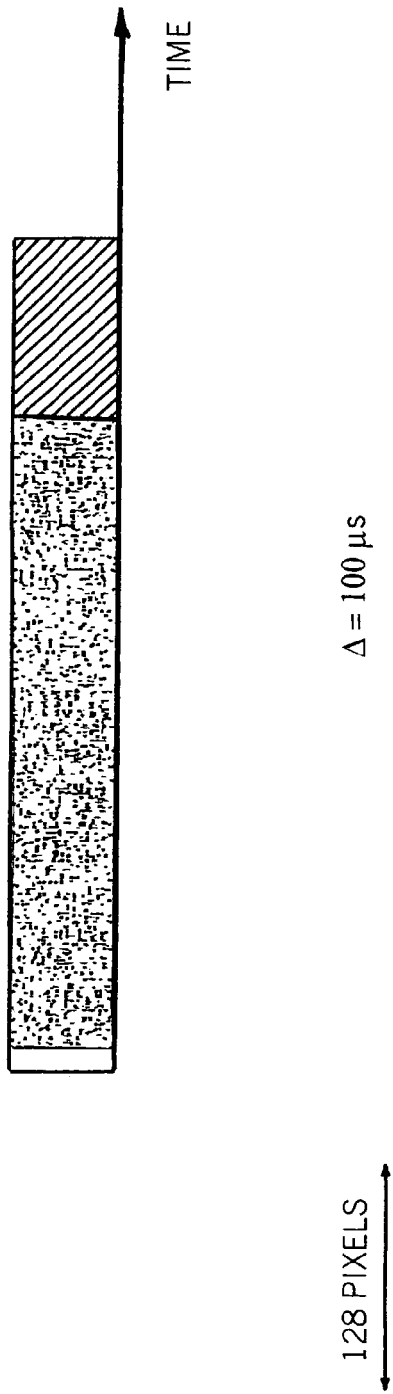
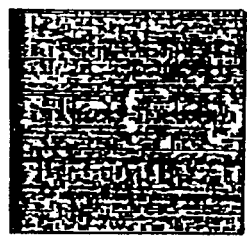
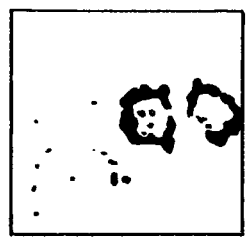
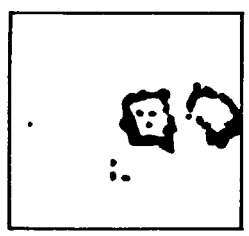
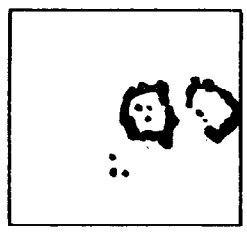
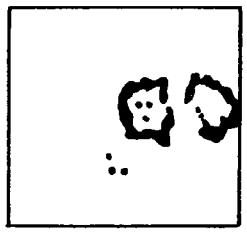
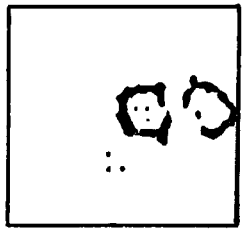

~60 MIN. AFTER SPORE RELEASE
<15 MIN. AFTER SPORE RELEASE
PRE-SPORE RELEASE

METHODS AND APPARATUS FOR ASSAYS OF BACTERIAL SPORES

CROSS-REFERENCE TO RELATED APPLICATIONS

The present application is a divisional of and claims priority to and the benefit of U.S. patent application Ser. No. 13/437,899 filed on Apr. 2, 2012, which is a continuation of U.S. patent application Ser. No. 11/810,005 filed on Jun. 4, 2007, issued as U.S. Pat. No. 8,173,359, which is a continuation of U.S. patent application Ser. No. 10/355,462 filed on Jan. 31, 2003 and now abandoned, which, in turn, claims priority to and the benefit of U.S. Provisional Application No. 60/353,268 filed on Feb. 1, 2002; U.S. Provisional Application No. 60/395,372 filed on Jul. 12, 2002; and U.S. Provisional Application No. 60/414,170 filed on Sep. 27, 2002, each of which are incorporated herein by reference in their entirety and to each of which priority is claimed pursuant to 35 USC 119.

The present application may also be related to U.S. Ser. No. 12/553,938 filed on Sep. 3, 2009, to U.S. Ser. No. 12/553,952 filed on Sep. 3, 2009 and issued as U.S. Pat. No. 9,469,866, to U.S. Ser. No. 11/453,296 filed on Jun. 13, 2006, to U.S. Ser. No. 11/404,382 filed on Apr. 14, 2006 and issued as U.S. Pat. No. 7,563,615, to U.S. Ser. No. 11/332,788 filed on Jan. 12, 2006 and issued as U.S. Pat. No. 7,611,862, to U.S. Ser. No. 10/987,202 filed on Nov. 12, 2004 and issued as U.S. Pat. No. 7,608,419, and to U.S. Ser. No. 10/306,331 filed on Nov. 27, 2002 and issued as U.S. Pat. No. 7,306,930.

STATEMENT REGARDING FEDERALLY SPONSORED RESEARCH OR DEVELOPMENT

The invention described herein was made in the performance of work under a NASA contract, and is subject to the provisions of Public Law 96-517 (35 USC 202) in which the Contractor has elected to retain title.

BACKGROUND OF THE INVENTION

1. Field of the Invention

The invention is directed assays of bacterial endospore levels.

2. Description of the Prior Art

The prior art for species-specific bacterial spore detection, using the lateral flow immunoassay method, is based on observing the red color of gold nanoparticles. It uses two antibodies, in combination, to specifically detect the bacterial spore species of interest in solution. One of the antibodies is attached to a colloidal gold nanoparticle, and the other antibody is immobilized on the nitrocellulose membrane downstream from the point of sample introduction. When about 100 µl of sample is added to the test strip membrane on top of the area 30 that contains the colloidal gold labeled antibodies, specific binding between bacterial spores and gold labeled antibodies occurs. Simultaneously, capillary action moves the gold labeled antibodies (both spore bound and not bound) along the strip membrane 32. In the sample region 34 of the test strip 32 (downstream), specific binding of a second antibody captures bacterial spores with the attached colloidal gold labeled antibody, which gives rise to a red line in the sample region 34 due to the immobilized gold nanoparticles as shown in the bottom left of FIG. 1. In the control region 36 of the test strip 32 (further downstream), as an internal control, a polyclonal antibody binds the gold labeled antibodies that did not bind bacterial spores of interest, which also gives rise to a red line. Thus, observation of two bands, one each in the sample and control regions, indicates a positive test for the bacterial spore of interest. The observation of only one band as shown in the bottom right of FIG. 1 is a negative test result. The fundamental limitation of this method is its sensitivity; a minimum concentration of $10^5$ spores/ml is needed before the red color from the gold nanoparticles becomes detectable; for reference, a 100 µl sample containing 10,000 anthrax spores is lethal.

Therefore what is needed is a method for improving the detection limit of lateral flow immunoassay based detection of bacterial spores, which is reported to be $10^5$ spores/ml. This prior art detection limit prevents detection of trace quantities of bacterial spores. A trace quantity of 8000 anthrax spores, for example, is enough fill a person.

The prior art the method for determining the fraction of viable bacterial spores is based on two measurements. First, the viable bacterial spore count is measured by colony counting, and second, the total bacterial spore count is measured by direct microscopic counting. The ratio of viable to total bacterial spore count yields the fraction of spores that remain viable within a given sample. The procedure for colony counting to determine endospore concentration is comprised of the steps of (1) heat shocking the sample to kill vegetative cells while bacterial spores remain viable, (2) plating a known volume of the sample with a known dilution factor onto a growth medium, and (3) incubating the growth plates for 2 days. Finally, the resulting visible colonies are counted and reported as colony forming units (CFU's). The procedure for direct microscopic counting is comprised of the steps of (1) placing the sample on a slide with an indentation of a known volume. The glass surface of the slide is inscribed with squares of known area. (2) The bacteria in each of the several squares are counted and the average count is multiplied by an appropriate factor to yield the number of total cells per milliliter in the original suspension.

These methods suffer prohibitive difficulties with low concentration samples collected in the field. First, bacterial spores tend to attach themselves onto particulates (dust etc.) and may easily represent the bulk of the biomass in a field sample. Unfortunately, attached bacterial spores cannot be counted with either colony counting or direct microscopic counting. Second, colony-counting methods only work for cultivable bacteria, which are in the minority in field samples (<10% of microbial species form colonies). Finally, the traditional methods are lengthy (>2 days) and labor intensive. These problems have made quantification of low concentration field samples extremely difficult, and have subsequently prevented the application of these methods towards a reliable and/or real-time bacterial spore live/dead assay.

There is a need to develop a live/dead assay for bacterial spores, because there is a need to measure the fraction of bacterial spores that remain viable for samples exposed to harsh environmental conditions such as desert and arctic environments. In terms of planetary protection, which is primarily concerned with spacecraft sterilization, in order to improve sterilization procedures, one must measure the fraction of viable spores after completion of various sterilization protocols. The samples of interest contain low bacterial spore concentration and many particulates, for which the prior art methods useless.

Prior art methods for monitoring aerosolized bacterial spores includes air filtering with subsequent PCR analysis of gene segments from species of interest, and aerosol sampling with subsequent culturing and colony counting. The PCR based method is strongly dependent on impurities in the air, such as city pollution, and requires specially trained technicians to perform sample preparation prior to running the PCR reaction. The procedure for colony counting, which is comprised of (1) heat shocking the sample to kill vegetative cells while bacterial spores remain viable, (2) plating a known volume of the sample with a known dilution factor onto a growth medium, (3) incubating the growth plates for two days, also requires the active participation of a technician. This also assumes that the spore forming microbes are cultivable. It is estimated that only 10% of bacterial species are cultivable. The cost of labor, technical complexity of PCR and slow response time of colony counting have prevented the wide spread application of these methods for monitoring of bacterial spores in the air.

SUMMARY

Synthesis of one form of a lanthanide complex according to the invention is shown in the embodiment diagrammed in FIG. 9 where ethylene diaminetetraacetic acid zwitterion (EZ) molecule is depicted. In refluxing ethanol (2-aminoethyl)trimethylammonium chloride hydrochloride is insoluble, however the free base (2-aminoethyl)trimethylammonium chloride, is soluble, and is generated in solution with sodium hydroxide. A metathesis reaction occurs, and fine microcrystals of sodium chloride precipitate from the hot ethanol mixture, leaving an ethanol solution of the freebase (2-aminoethyl)trimethylammonium chloride. To this solution is added ethylene diamine tetra-acetic acid (EDTA) dianhydride, which reacts with the primary amine group of the two equivalents of (2-aminoethyl)trimethylammonium chloride. This reaction yields EZ in its carboxylic acid form. To produce the zwitterionic form of EZ, two extra equivalents of the free base amine are added to deprotonate this intermediate carboxylic acid yielding EZ and (2-aminoethyl)trimethylammonium chloride hydrochloride which is insoluble in ethanol and easily filtered away from the solution. It must be understood that many other forms and syntheses of lanthanide ions in the form of lanthanide complex are possible and expressly contemplated as being within the scope of the invention. Each of the alternative forms will combine with the medium as an analysis reagent which is capable of cooperative binding with dipicolinic acid from endospores to increase both the lanthanide-dipicolinic acid binding constant and the luminescence quantum yield.

The enhancement in the binding of a DPA molecule to the Tb3+ is the result of several factors at play in the ternary complex of a DPA molecule, a Tb3+ ion and EZ molecule. First the EZ molecule acts as a template or foundation capturing a Tb3+ with the amine and carboxylate groups at the core of the molecule to yield a complex (EZ-Tb) 3+. Notice that the overall charge of this complex is 3+, but that two units of charge have effectively migrated out to the trimethylammonium groups at the ends of the molecule, which are not involved in the coordination of the EZ molecule to the Tb3+ ion. FIG. 10 is a graph of the experimental data showing the enhanced intensity in detection of DPA (M) using the EZ molecule to complex with Tb.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

Lateral Flow Immunoassay

One embodiment of the invention is defined as a method for lateral flow immunoassay for bacterial spore detection and quantification comprising the steps of providing a matrix including terbium ions, releasing DPA from the bacterial spores, combining the terbium ions with the DPA in solution, and exciting the combined terbium ions and DPA to generate a luminescence characteristic of the combined terbium ions and DPA to detect the bacterial spores. The detection of the spores or their concentration above a predetermined threshold generates an alarm signal.

The DPA is released from the bacterial spores by microwaving the spores, germinating the spores with L-alanine, sonicating the spores with microspheres or autoclaving the spores. These methods by no means necessarily exhaust the ways in which the DPA can be released from the spores and all other methods of lysing the spores are deemed equivalent.

Exciting the combined terbium ions and DPA generates a luminescence characteristic of the combined terbium ions and DPA. This is achieved by radiating the combined terbium ions and DPA with ultraviolet light. Again, any method by which luminescence can be induced is included within the scope of the invention and is deemed to be equivalent.

The invention can also be characterized as a method for lateral flow immunoassay for bacterial spore detection and quantification. The method starts with the step of adding a sample of unknown bacterial spores to a test strip. The sample of unknown bacterial spores is drawn to a first sample region on the test strip by capillary action. Species-specific antibodies are bound to the sample when the unknown bacterial spores match the species-specific antibodies, otherwise the sample is left unbound. DPA is released from the bacterial spores in the bound sample. The terbium ions are combined with the DPA to form a Tb-DPA complex. The combined terbium ions and DPA are excited to generate a luminescence characteristic of the combined terbium ions and DPA to detect the bacterial spores.

The method further comprises the steps of performing the same steps with a standard of known bacterial spores with known concentration. The sample is added to the test strip and drawn to a second sample region on the test strip. Species-specific antibodies are selectively bound to the standard when the known bacterial spores match the species-specific antibodies, otherwise the standard unbound is left unbound. DPA is released from the bacterial spores in the bound standard and combined with the terbium ions. The combined terbium ions and DPA are excited to generate a luminescence characteristic of the combined terbium ions and DPA to detect the bacterial spores of the standard. The intensity of the excited luminescence from the sample is compared with the excited luminescence from the standard to derive a quantification of the spore concentration in the sample. The method may further comprise the step of confirming arrival of the sample and standard in the first and second sample regions respectively by means of a visual indicator.

Live/Dead Assay for Bacterial Spores

The invention is defined in another embodiment as a method for live/dead assay for bacterial spores comprising the steps of: providing a solution including terbium ions in a sample of live and dead bacterial spores; releasing DPA from viable bacterial spores by germination from a first unit of the sample; combining the terbium ions with the DPA in solution released from viable bacterial spores; exciting the combined terbium ions and DPA released from viable bacterial spores to generate a first luminescence characteristic of the combined terbium ions and DPA to detect the viable bacterial spores; releasing DPA from dead bacterial spores in a second unit of the sample by autoclaving, sonication or microwaving; combining the terbium ions with the DPA in solution released from dead bacterial spores; exciting the combined terbium ions and DPA released from dead bacterial spores to generate a second luminescence characteristic of the combined terbium ions and DPA to detect the dead bacterial spores; generating a ratio of the first to second luminescence to yield a fraction of bacterial spores which are alive.

Lifetime-Gated Measurements of Bacterial Spores and Imaging Bacterial Spores Using an Active Pixel Sensor In yet another embodiment the invention is a method for lifetime-gated measurements of bacterial spores to eliminate any fluorescence background from organic chromophores comprising the steps of providing a solution including terbium ions with a sample of bacterial spores; labeling the bacterial spore contents with a long-lifetime lumophore; releasing DPA from the bacterial spores; combining the terbium ions with the DPA in solution; exciting the combined terbium ions and DPA for a first time period; waiting a second time period before detecting luminescence; and detecting a luminescence characteristic of the combined terbium ions and DPA after the second time period during a defined temporal window synchronized with luminescence timed from the long lifetime lumophore to detect the bacterial spores.

In one embodiment the first time period of excitation is of the order of nanoseconds, the second time period is of the order of microseconds and the defined temporal window is of the order of milliseconds.

In another embodiment the first time period of excitation is of the order of 1-10 nanoseconds, where the second time period is of the order of tens of microseconds and where the defined temporal window is of the order of 1-10 milliseconds.

In still another embodiment the first time period of excitation is of the order of nanoseconds, the second time period is of the order of tenths to tens of milliseconds and where the defined temporal window is of the order of hundreds of microseconds.

Unattended Monitoring of Bacterial Spores in the Air

In yet another embodiment the invention is a method for unattended monitoring of bacterial spores in the air comprising the steps of collecting bacterial spores carried in the air; suspending the collected bacterial spores in a solution including terbium ions; releasing DPA from the bacterial spores; combining the terbium ions with the DPA in solution; exciting the combined terbium ions and DPA to generate a luminescence characteristic of the combined terbium ions and DPA; detecting the luminescence to determine the presence of the bacterial spores; and generating an alarm signal when the presence of bacterial spores is detected or the concentration thereof reaches a predetermined magnitude.

The step of collecting bacterial spores carried in the air comprises capturing the bacterial spores with an aerosol sampler or impactor. The step of detecting the luminescence to determine the presence of the bacterial spores comprises monitoring the luminescence with a spectrometer or fluorimeter.

Preferably, the step of collecting bacterial spores carried in the air comprises continuously sampling the air and the step of detecting the luminescence to determine the presence of the bacterial spores comprises continuously monitoring the luminescence.

When the step of releasing DPA from the bacterial spores comprises microwaving the bacterial spores to heat the solution, the step of combining the terbium ions with the DPA in solution comprises cooling the heated solution to increase the fraction of bound Tb-DPA complex.

The invention is also apparatus for performing the various methods disclosed above. For example, the invention includes an apparatus for unattended monitoring of bacterial spores in the air comprising: a biosampler for capturing the bacterial spores in the air and having a collection vessel containing a solution including terbium ions into which the captured bacterial spores are suspended; means for releasing DPA from the bacterial spores in the solution to allow the DPA to combine with the terbium ions to form a Tb-DPA complex; an energy source for exciting the Tb-DPA complex to generate luminescence; an electro-optical circuit to measure the luminescence; and an alarm circuit coupled to the electro-optical circuit to detect a bacterial spore concentration above a predetermined threshold.

The invention is also an apparatus for lateral flow immunoassay for bacterial spore detection and quantification comprising: a strip of material for providing lateral capillary flow of a solution including terbium ions across the strip; an input region on the strip for receiving a liquid sample containing terbium ions, the first zone being provided with a first antibody for specific binding to a specific specie of bacterial spores; a sample region of the strip laterally displaced from the input region and communicated thereto by means of capillary flow therebetween, the sample region being provided with a second antibody to capture bacterial spores with the attached first antibody and to immobilize them; means for releasing DPA from the bacterial spores in the sample region of the strip to then allow the terbium ions to combine with the DPA in solution; an energy source to excite the combined terbium ions and DPA in the sample region of the strip to generate a luminescence characteristic of the combined terbium ions and DPA; and a luminescence detector to identify the presence or measure the concentration of the bacterial spores in the sample region of the strip.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 3 is a diagrammatic illustration showing a few drops of bacterial spore containing sample are added to the test strip membrane.

FIG. 4a shows the intensity during germination starting with t=0 when L-alanine was added. FIG. 4b shows the Tb luminescence after completion of germination corresponding to Tb-DPA complex. FIG. 4c shows Tb luminescence induced by autoclaving.

FIG. 5a-5b shows a diagram and related images illustrating the active pixel sensor imaging method as applied to Tb luminescence in bacterial spores.

FIG. 8a illustrates the time course of spore monitoring and FIG. 8b shows the spectrum just before spore release, less than 15 minutes after spore release and 60 minutes after spore release.

FIG. 9 is a diagram of the synthesis of an ethylene diaminetetraacetic acid zwitterion (EZ) molecule.

FIG. 10 is a graph of the experimental data showing the enhanced intensity in detection of DPA (M) using the EZ molecule to complex with terbium (Tb).

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Lateral Flow Immunoassay

The invention is directed to lateral flow immunoassay for bacterial spore detection and quantification using lanthanide luminescence with both high sensitivity and selectivity in less than five minutes. The method combines lateral flow immunoassay and dipicolinic acid (DPA) triggered terbium (Tb) luminescence technologies. The lateral flow immunoassay provides high selectivity for specific bacterial spore species, and the DPA triggered Tb luminescence method for bacterial spore detection enables greatly improved detection limits over the prior art detection schemes.

The new technology has significantly improved detection limits, because it is based on Luminescence turn-on against a dark background, which is much more sensitive than measuring the scattered light, from gold nanoparticles against a bright background. Based on DPA-triggered Tb luminescence experiments, we anticipate single spore detection limits for 100 μl samples (i.e. 10 spores/ml).

The solution for developing a lateral flow immunoassay based detection of bacterial spores with single spore detection limits is to use DPA triggered Tb luminescence as the detection scheme. The methodology for achieving single spore detection is more expressly disclosed in U.S. patent application Ser. No. 10/306,331 filed on Nov. 27, 2002, entitled "An Improvement In A Method For Bacterial Endospore Quantification Using Lanthanide Dipicolinate Luminescence," and assigned to the same assignee as the present invention, which application is incorporated herein by reference, and issued as U.S. Pat. No. 7,306,930 on Dec. 11, 2007 entitled "Method Bacterial Endospore Quantification Using Lanthanide Dipicolinate Luminescence".

Consider now the DPA-triggered Tb luminescence detection of bacterial spores. Dipicolinic acid DPA, 2,6 pyridinedicarboxylic acid) is present in high concentrations (about 1 molar or about 15% of by weight) in the core of bacterial spores 38 as a 1:1 complex with $Ca^{2+}$ as shown in FIG. 2*a*. For all known lifeforms, DPA is unique to bacterial spores and is released into bulk solution upon germination, which is the process of spore-to-vegetative cell transformation. Thus, DPA is an indicator molecule for the presence of bacterial spores. Fortuitously, DPA is also a classic inorganic chemistry ligand that binds metal ions with high affinity. DPA binding to terbium ions triggers intense green luminescence under UV excitation as shown in FIGS. 2*b* and 2*c*. Thus, the green luminescence turn-on signals the presence of bacterial spores, and the intensity of the luminescence can be correlated to the number of bacterial spores per milliliter. Potential interferents such as sugars, nucleic and amino acids are present in much lower concentrations in endospores and vegetative cells and have binding constants for Tb that are approximately six orders of magnitude less than that of DPA ($K_A=10^{8.7}$ $M^{-1}$). This method is relatively immune to these interferents.

The core of bacterial spores contains 1 molar dipicolinic acid (DPA) (~15% of the spore dry weight). It has been shown that the DPA can be released into bulk solution by microwaving the sample (germination with L-alanine, sonication with microspheres, and autoclaving have also been used to release DPA from the spore). When the released DPA binds terbium ions in bulk solution, bright green luminescence is triggered under UV excitation.

The mechanism of DPA-triggered Tb luminescence is based on the unique photophysical properties of lanthanide ions. The luminescence of lanthanide ions is characterized by long lifetimes (0.1 to 1 ms), small extinction coefficients (a.k.a. absorbtivity, about 1 $M^{-1}$ $cm^{-1}$) and narrow emission bands. These characteristics arise because the valence f orbitals are shielded from the environment by the outer 5s and 5p electrons, and because the transition between the emitting excited stare and ground state is highly forbidden. Thus, direct excitation of terbium ions leads to weak luminescence due to the small absorption cross section. However, coordination of aromatic chromophores, like DPA, triggers intense terbium luminescence. The juxtaposition of DPA, which has an absorbtivity of 5000 $M^{-1}$ $cm^{-1}$ serves as a light-harvesting center (e.g. antenna effect). Strong electronic coupling and downhill energies allow the DPA centered excitation energy to be efficiently transferred to the lanthanide ion, which subsequently luminesces bright green.

Figure 1:
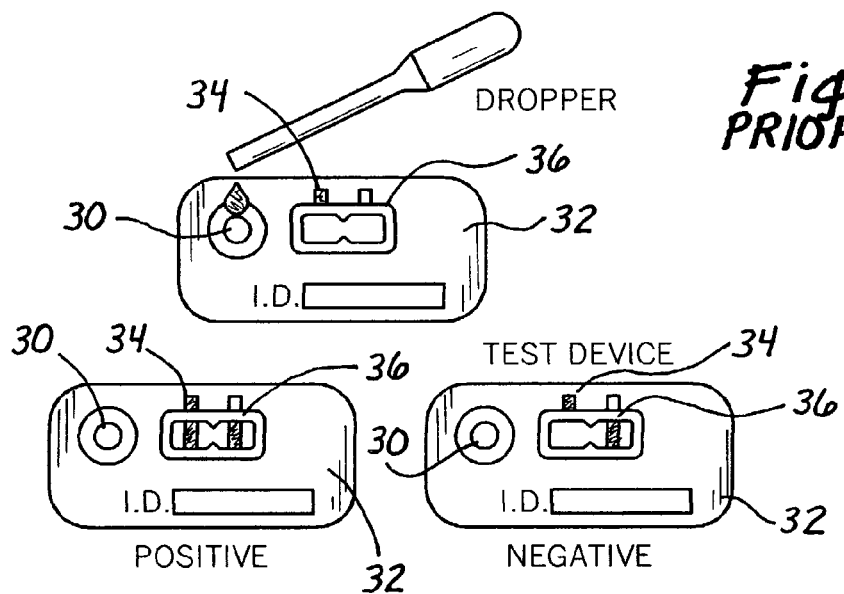
FIG. 1 is a diagram of a prior art lateral flow immunoassay for bacterial spores.
Figure 2A:
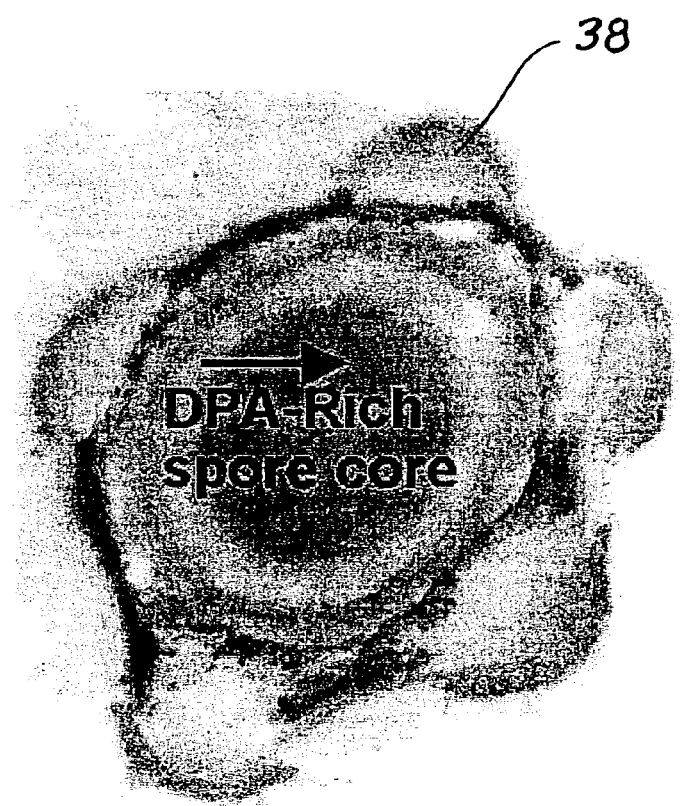
FIG. 2a is a microscopic image of a spore (about 1 μm in diameter) highlighting a DPA rich spore core.
Figure 2B:
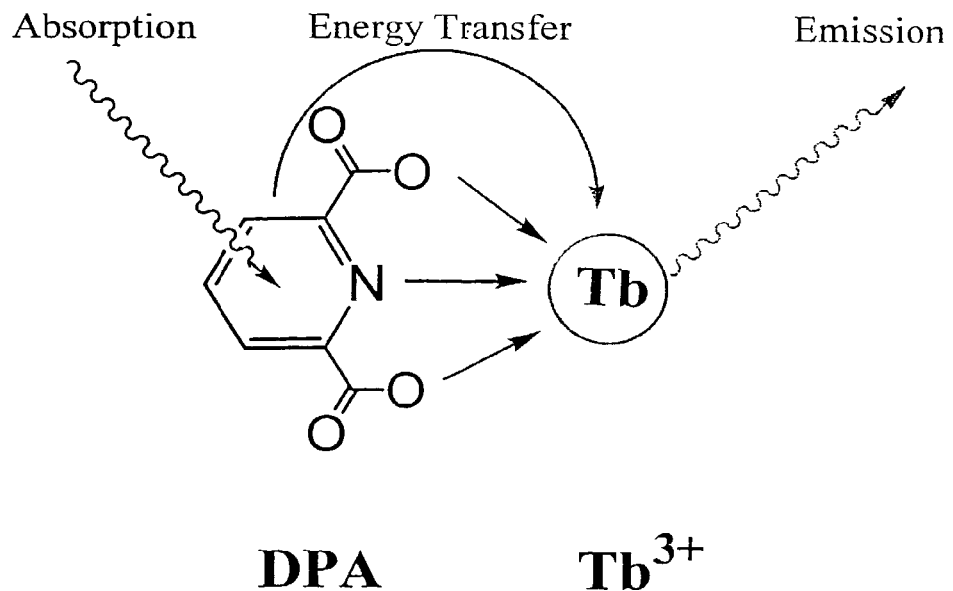
FIG. 2b is a diagram of a $Tb^{3+}$ ion (shaded ball) by itself has a low absorption cross section (<10 $M^{-1}$ $cm^{-1}$ and consequently has low luminescence intensity. The $Tb^{3+}$ ion can bind the light harvesting DPA (absorption cross section >$10^4$ $M^{-1}$ originating from the spore; DPA binding gives rise to bright Tb luminescence.
Figure 2C:
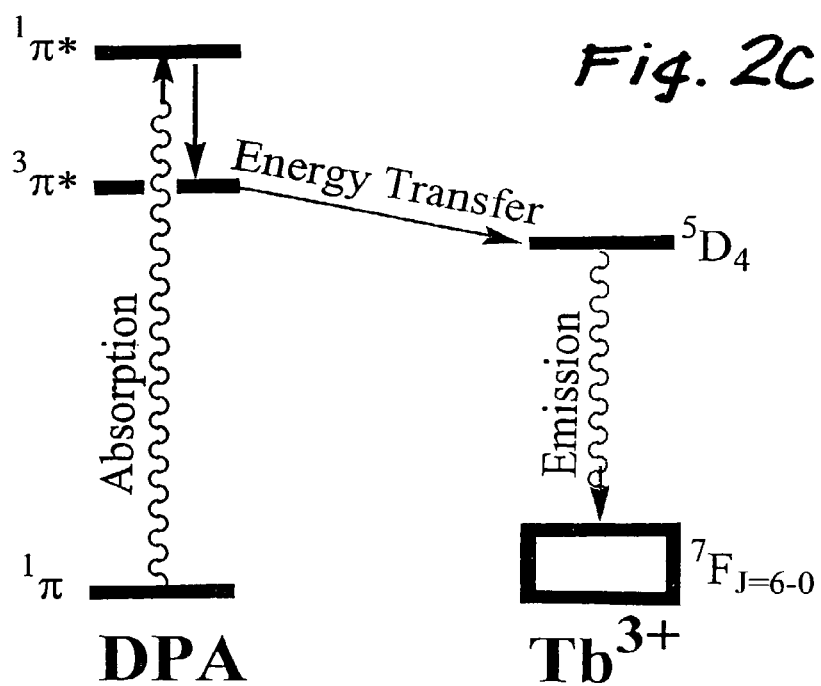
FIG. 2c is a diagram of a photophysical scheme for DPA sensitized luminescence of the Tb complex (absorption-energy transfer-emission, AETE).
Figure 4A:
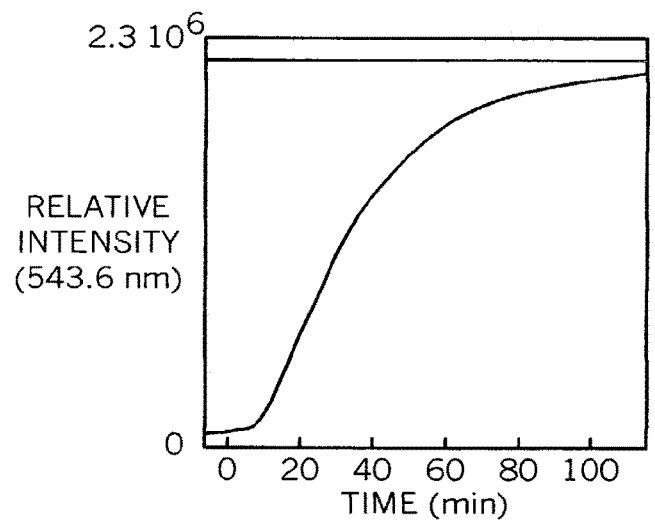
FIGS. 4a-4c are graphs of the intensity of Tb luminescence verses time.
Figure 4B:
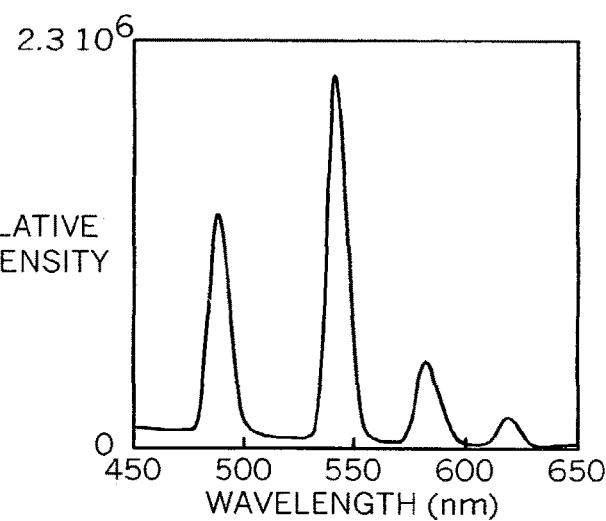
Figure 4C:
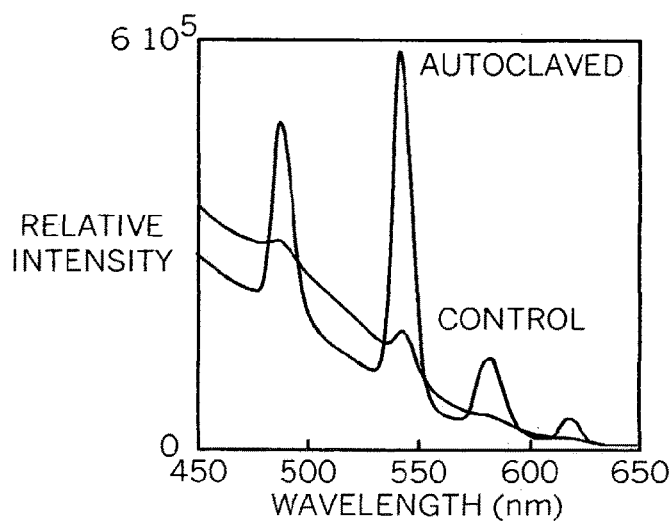

Consider now the details of lateral flow immunoassay with DPA-triggered Tb luminescence detection of bacterial spores 10. The test strip 18 is comprised of a nitrocellulose membrane 12 that has species-specific antibodies bound in the sample regions, which are regions 26 and 22 of the strip as shown in FIG. 3. Region 26 contains antibodies for the bacterial spore species 10 of interest (e.g. *B. anthracis* antibody), and region 22 contains antibodies for *B. subtilis* (standard 20). First, about 100 μl of sample 10 in a liquid, such as water, and standard 20 in a solution of the same or a different liquid are added to their respective test strip membranes 12 and 16 in the sample port region 30. Capillary action moves the spores 10 along the strip membrane 12 and 16. In the sample region 14 of the test strip 12 (downstream), specific binding of membrane-bound antibodies captures and immobilizes the bacterial spores 10, while components of the sample 10 that do not bind the antibody continue to flow out of the sample region 14. Regions 24 contain an indicator, such as cobalt chloride, that changes visible color when the liquid or solvent front arrives, after about five minutes, which should suffice to provide adequate separation of the specific binding components to the non-specific components of the sample 10. For example, where the indicator is cobalt chloride, the color changes to blue to pink on arrival of the liquid, which is in this embodiment is water. The choice of liquid and indicator is a matter of design choice and many other selections can be equivalently substituted. In the next step, DPA is released from the core of the spores 10 by microwaving the test strip 12. The released DPA binds Tb dissolved in the solution and triggers green luminescence, which signals the presence of bacterial spores. The green luminescence can be read or measured by a conventional spectrometer or fluorometer (not shown).

The control is performed on a parallel test strip to which about 100 μl containing a known concentration of *Bacillus subtilis* is added. The standard 20 undergoes the identical procedure as the unknown sample 10. Green luminescence in region 22 and a change in color in regions 24 indicates that the assay has worked properly and the ratio of luminescence intensity from the sample 10 in region 26 and standard 20 in region 22 is proportional to the concentration of the bacterial spore of interest. The microwaving step can be completed in less than 2 minutes. Thus the complete assay can be performed within 7 to 10 minutes. The sample 10 and standard 20 may be processed simultaneously or sequentially as may be desired.

Live/Dead Assay for Bacterial Spores

The invention also includes a method and apparatus to measure the fraction of bacterial spores that remain viable or alive, hence a live/dead assay for bacterial spores. The method combines dipicolinic acid triggered terbium luminescence and dipicolinic acid release from (1) viable bacterial spore through germination, and (2) all viable and nonviable bacterial spores by autoclaving, sonication, or microwaving. The ratio of the results from steps (1) and (2) yield the fraction of bacterial spores that are alive.

The invention does not suffer from the aforementioned prior art problems of colony or microscopic counting, because it is based on a molecular approach that (1) works whether or not a bacterial spore is attached on a particulate, (2) does not require bacteria to be cultivable, and (3) can be performed on the timescale of 20 minutes.

The solution for developing a live/dead assay for bacterial spores requires a molecular approach. DPA can be released into bulk solution by inducing germination with L-alanine or by autoclaving the sample. In germination, only viable spores release DPA, while autoclaving forces all spores, viable and nonviable, to release DPA. Microwaving and sonication also releases DPA from all spores, whether dead or alive. Again, when the released DPA binds terbium ions in bulk solution, bright green luminescence is triggered under UV excitation.

The luminescence intensity can be correlated to the concentration of viable bacterial spores when germination is used to release the DPA, and to the total bacterial spore concentration when either autoclaving, sonication, or microwaving is used to release DPA. Thus, these methods of DPA release allow us to quantify both the viable and total bacterial spore count, and subsequently the fraction of spores that are viable for a given sample.

Since germination releases the DPA content of viable bacterial spores, while autoclaving, sonication, and microwaving releases the DPA content of all bacterial spores, including non-viable bacterial spores, using the DPA triggered Tb luminescence method in conjunction with the DPA release, induced by (1) germination and (2) either autoclaving, sonication, and microwaving, allows us to determine the viable and total spore count, respectively, and subsequently the fraction of viable bacterial spores as illustrated in FIGS. 4*a*, 4*b* and 4*c*. FIG. 4*a* shows the time course data of endospore germination monitored by DPA triggered Tb luminescence at 543 nm. Time zero corresponds to L-alanine induced germination. FIG. 4*b* shows the spectrum of the luminescence corresponding to Tb-DPA complex, which is induced after completion of germination. FIG. 4*c* compares the spectrum for an autoclaved sample verses a control sample which is not autoclaved.

Lifetime-Gated Measurements of Bacterial Spores and Imaging Bacterial Spores Using an Active Pixel Sensor Finally, the method of the invention is amenable to lifetime-gated measurements to eliminate any fluorescence background from organic chromophores. It is also possible to quantify the fraction of bacterial spores that remain viable by inducing DPA release by germination and microwaving as described below, and to obtain further increased sensitivity by preparing special Tb complexes that enhance the luminescence turn-on, and DPA binding affinity.

Consider now the problem of imaging bacterial spores. The imaging methodology is again based on a combination of dipicolinic acid triggered terbium luminescence (Tb luminescence assay) and imaging using an active pixel sensor (APS), which is well known to the art. The Tb luminescence assay enables specific detection of bacterial spores with a current detection limit of 5,000 spores/ml when $TbCl_3$ used as the analysis reagent. This assay can be performed in 30 minutes or less depending on the DPA release mechanism that is employed. APS is ideally suited to image the resultant Tb luminescence when spores are present because of its inherent ability to perform lifetime gated imaging.

In this embodiment the spores or their contents have been labeled with a long-lifetime lumophore which fact is used to advantage during detection. Since almost every natural fluorescent material decays in a few nanoseconds, delayed luminescence is a powerful discriminator against background biological or mineralogical signals. For example, flavinoids, NADH, collagen and many other biological and cellular components fluoresce in the wavelength region of 300-500 nm, but all have lifetimes less than a few tens of nanoseconds.

Jet Propulsion Laboratory has developed a true snapshot imager, using CMOS technology in an APS that is ideally suited for imaging and measurement of delayed luminescence probes. In this implementation, the entire imager can be cycled off and on in a clock cycle, typically less than a microsecond. The basic measurement cycle is to pulse an excitation source for the luminescence with an on time of a few nanoseconds, wait 30 µs and then turn on the imager for 2 ms, turn it off and read out the image and the photon counts for each pixel. A unique feature of the CMOS or Active Pixel Sensor (APS) technology is that each pixel can contain active circuit elements and can perform signal averaging to improve the signal to noise as well as other processing. By imaging the collection tape, we can count the pixels that contain luminescence signal and get a spore count.

Figure 6:
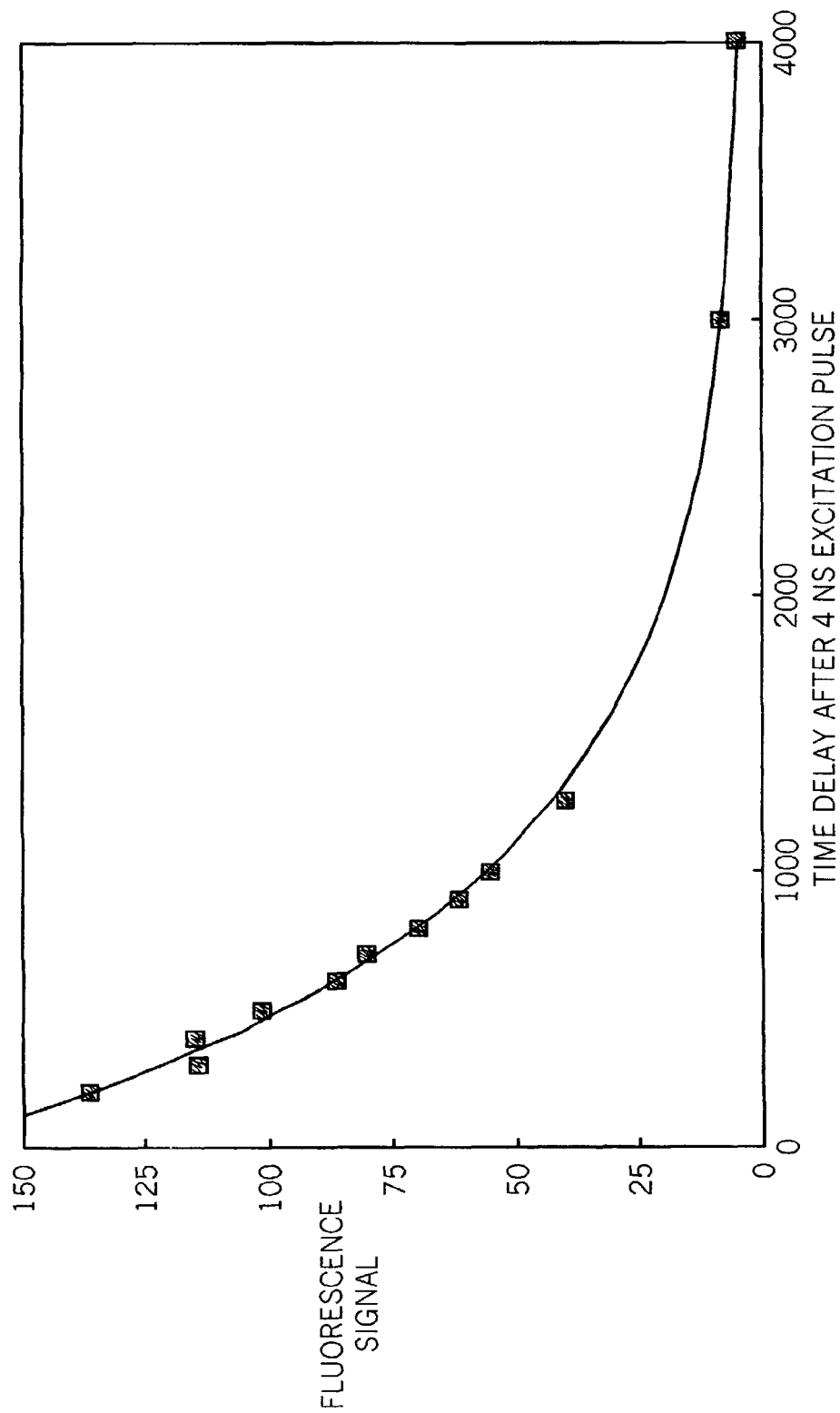
FIG. 6 is the lifetime series decay of the bacterial spores illuminated in FIG. 5.

FIG. 5a shows a diagrammatic timing sequence for excitation, a delay φ, and detector integration time Δ. Image data taken with the APS for an Europium probe with a lifetime of ~800 J.JS is shown in FIG. 5b in which we applied a few spots of the Europium probe to an APS 256×256 imager and excited the fluorescence with a pulsed $N_2$ laser at 337 nm and a pulse width of ~4 ns. Excitation can be performed with a compact laser, laser diode or LED. By adjusting the timing of the detection window, delay φ, the decay curve of the fluorophore can be mapped out as shown in FIG. 6, which is a graph of the lifetime data obtained from the images of FIG. 5b. The fluorescence signal in FIG. 6 is summed up from all the pixels on the upper spot of the APS sensor as shown in FIG. 5b.

Unattended Monitoring of Bacterial Spores in the Air

Consider now the technology that is required to enable one to achieve unattended monitoring of bacterial spores in the air. The novelty of the method lies again in the combination of (1) aerosol capture methods and (2) lanthanide luminescence detection of bacterial spores. This combination will enable an alarm for airborne bacterial spores similar in concept to a smoke detector, which works continuously and unattended.

The invention as described below does not suffer from the above mentioned problems of the prior art, because it (1) does not require cultivable bacteria, and (2) can be performed continuously with a sampling rate of at least four readings per hour using current instrumentation, and (3) does not require active sampling by a trained technician.

Online monitoring of aerosolized bacterial spores, such as *Bacillus anthracis* and *Clostridium* botulism spores, is essential in locations such as public transportation, mail sorting, food preparation, health care facilities and even military environments. We have become especially motivated to develop a method of unattended monitoring of bacterial spores in the air after the anthrax attacks following the Sep. 11, 2002 terrorist attacks. Another motivation was the application of the method towards planetary protection, which is primarily concerned with spacecraft sterilization.

A solution for unattended monitoring of airborne bacterial spores is achieved by the combination of (1) aerosol capture methods and (2) lanthanide luminescence detection of the bacterial spores as described above. The luminescence intensity arising from DPA detection can be correlated to the concentration of bacterial spores. When this detection method is coupled to an aerosol capture device that suspends aerosolized spores into a terbium containing solution, unattended monitoring of bacterial spores in the air is enabled. In general, the method comprises the steps of capturing aerosolized bacterial spores with an aerosol sampler or impactor of which there are many commercial models are available. The captured spores are then lysed using microwave radiation, autoclaving, or other methods that release DPA from the core of the spores. The released DPA then binds terbium ions or other chromophores that give rise to luminescence turn-on upon DPA binding. The luminescence turn-on is monitored by a luminescence spectrometer or fluorimeter. Continuous sampling of the air while monitoring for luminescence turn-on gives rise to an alarm capability for aerosolized bacterial spores, which does not require human participation over extended periods, such as time periods of the order of 8 hours.

Figure 7:
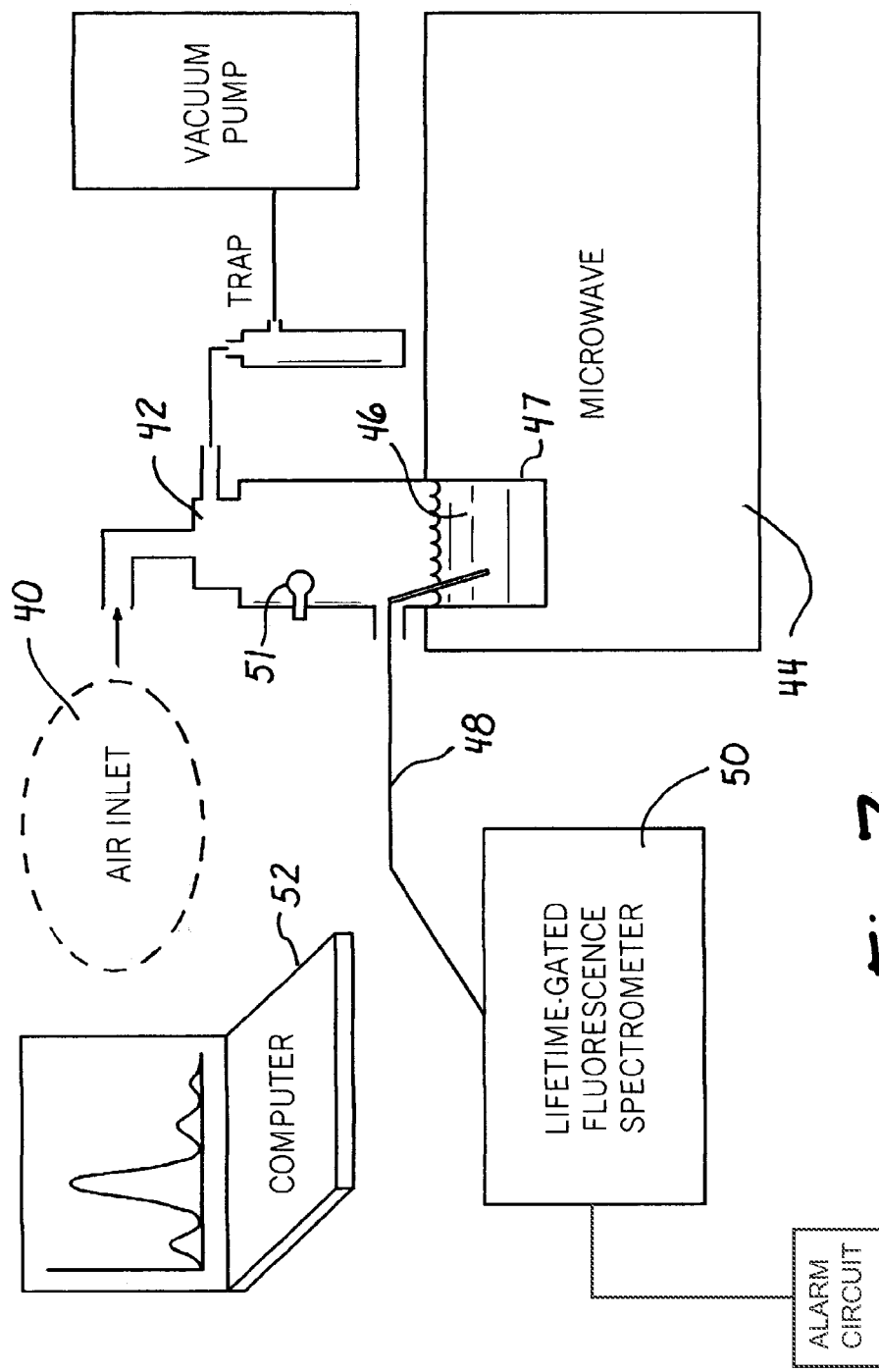
FIG. 7 is a simplified diagram of an unattended air monitor for bacillus using Tb-DPA detection.

In the illustrated embodiment stock solutions of purified *Bacillus subtilis* spores were purchased from Raven Biological. A Lovelace nebulizer was used to generate an aerosol 40 of the bacterial spore air suspensions. The spore "smoke" detector instrument as shown in the diagram of FIG. 7, is comprised of three components: (1) a biosampler 42 for aerosol capture, (2) a microwave with temperature and pressure control 44 for releasing the DPA from the spores, and (3) a lifetime-gated luminescence spectrometer 50 for luminescence detection. The lifetime gating works by exciting the sample with a short Xe-lamp flash 51 and waiting several microseconds before detecting light from the sample 46, thus eliminating the background fluorescence from impurities with 10-ns fluorescent lifetimes.

The biosampler 42, filled with 20 ml of 10 µM $TbCl_3$ glycerol solution, has a 95% transfer efficiency for microbe-containing aerosols. Once bacterial spores are suspended in the biosampler collection vessel 47, microwaving completely or sufficiently releases DPA into bulk solution 46 within 8 minutes or less. The resulting free DPA then binds Tb in bulk solution, giving rise to luminescence turn-on under UV excitation. A fiber optic probe 48 immersed in the sample solution transmits the Luminescence to the spectrometer 50. Spectrometer 50 is coupled to alarm circuit 52 which then generates an appropriate alarm signal when a predetermined detection occurs, namely a wireless or wired signal with identification information is generated and transmitted to a remote monitoring station. The monitoring station may monitor a plurality of remote biosensors such as shown in FIG. 7 and providing a continuous time, date, place and biomeasurement report from them.

Figure 8A:
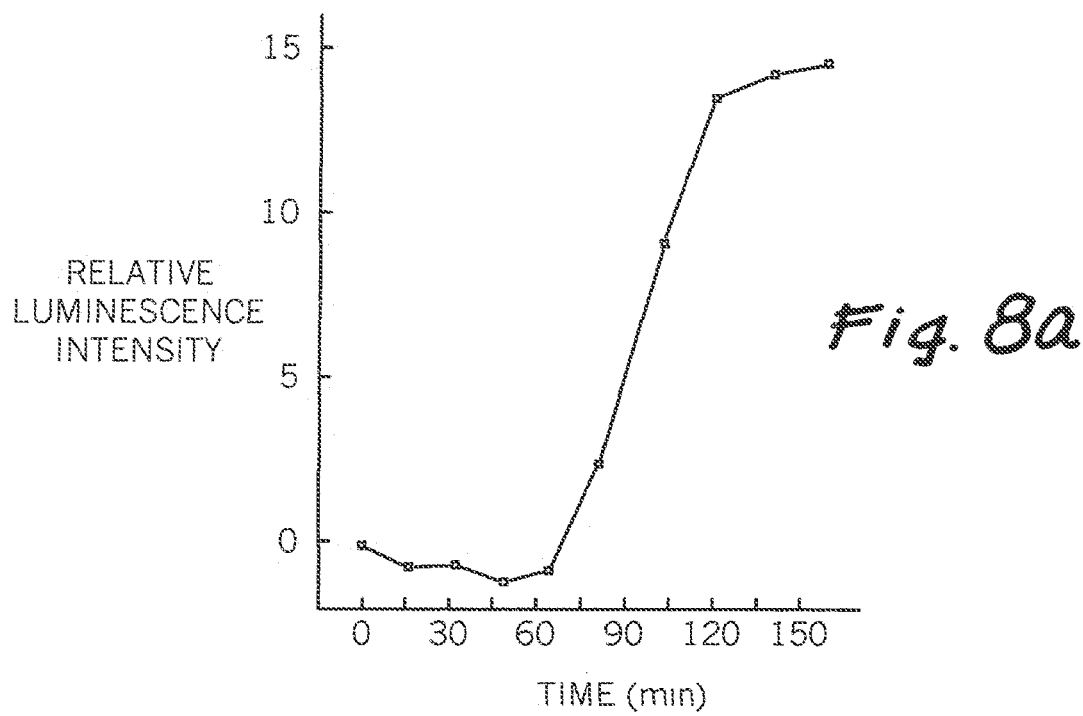
FIGS. 8a and 8b are graphs of the relative luminescence intensity as a function of time and wavelength respectively.

While the biosampler 42 is continually sampling the air, a cycle comprising an 8-minute microwaving step at 140° C. at 1 atmosphere, a 7 minute cooling period, and a 30 second luminescence measurement is performed repeatedly. Cooling down to room temperature is required because the binding constant for the Tb-DPA complex at 140° C. is much lower than at room temperature, thus leading to near zero fraction bound at 140° C. FIG. 8a shows the time course of the luminescence intensity at 543.5 nm versus time for the online monitoring for aerosolized bacterial spores in the device of FIG. 7. After five data points are collected in the time interval between t=0 and 63 minutes, we initiated the nebulizer for 5 minutes to generate aerosolized bacterial spores, which were directed to the inlet of the biosampler 42. The sixth data point at t=81 min clearly shows the presence of Tb-DPA luminescence, thus signaling the presence of bacterial spores. The luminescence intensity in the plateau region after 130 minutes corresponds to a spore concentration of $10^5$ spores/mi. The luminescence increases for two more heating and cooling cycles and then plateaus 60 minutes after the initiation of the spore event.

Figure 8B:
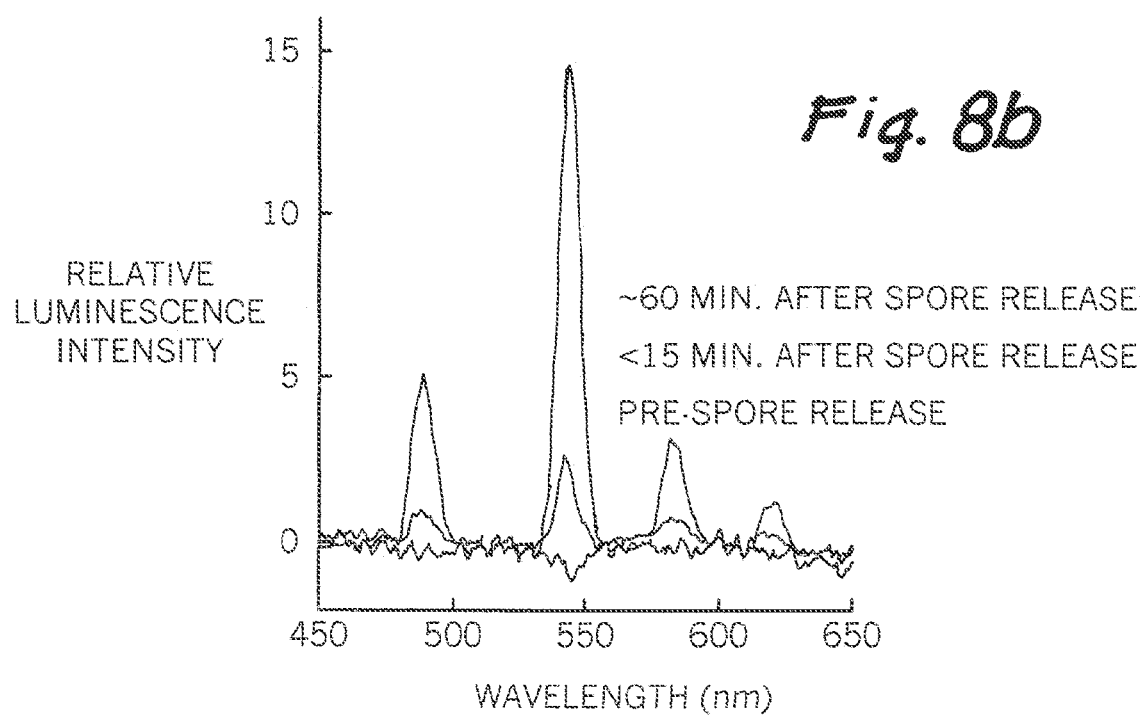
Figure 9:
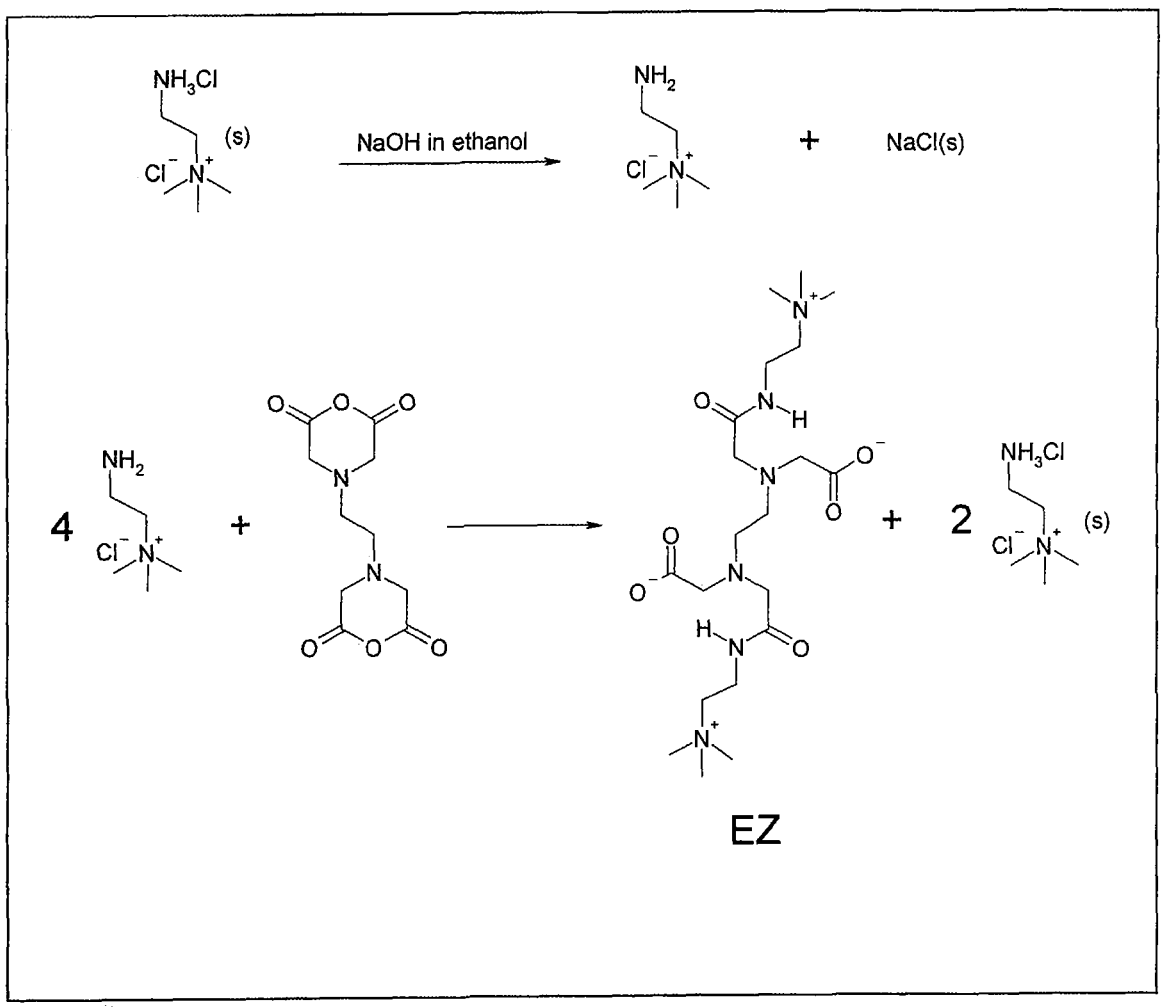
Figure 10:
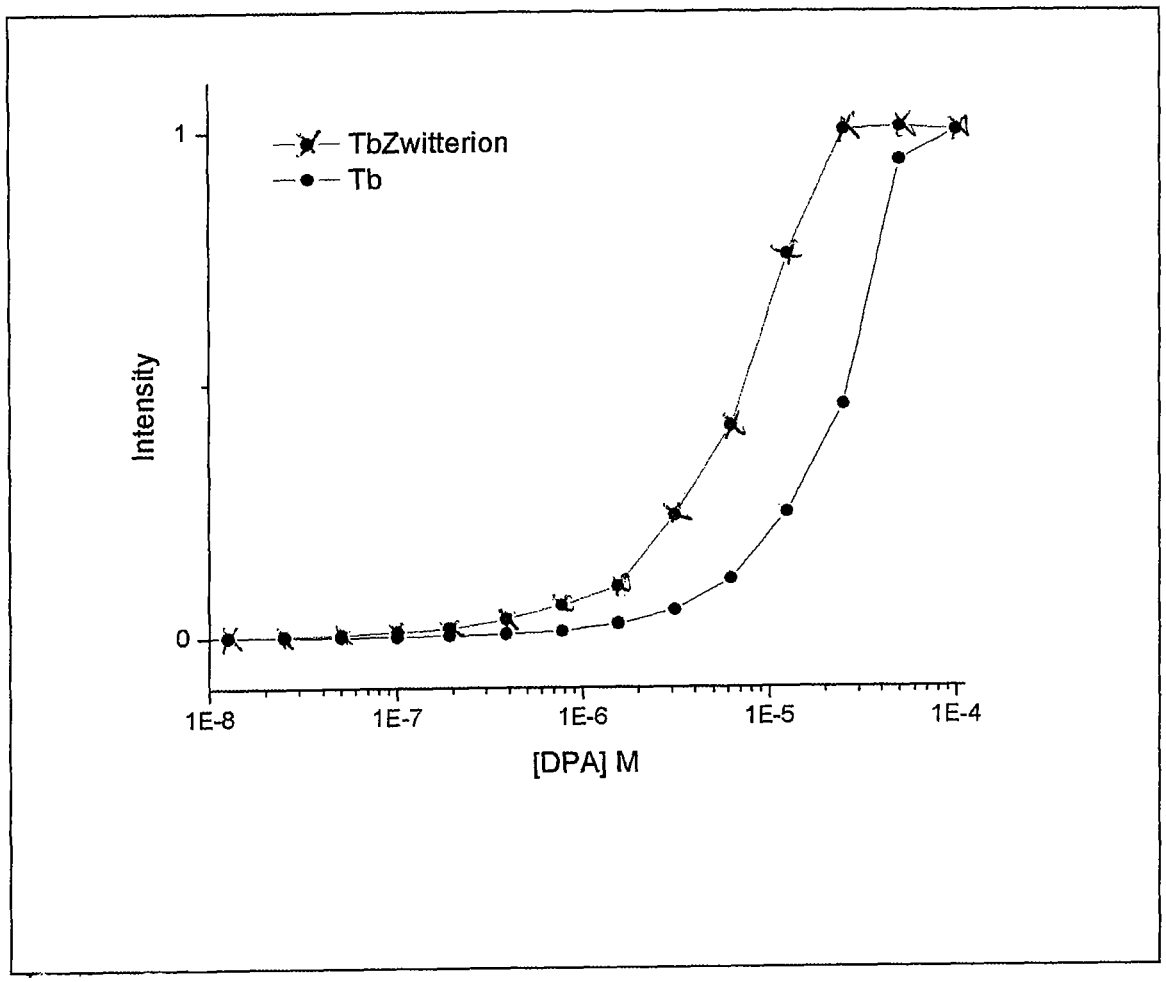

FIG. 8b shows the luminescence spectra before and after the generation of aerosolized bacterial spores. Clearly, the signal-to-noise ratio of 10, one cycle after spore introduction, shows that we can detect aerosolized spores with a response time of about 15 minutes. Spore lysing methods, such as sonication with microbeads, that do not require high temperature will lead to increased sampling rates.

Thus, we have demonstrated quantification of aerosolized bacterial spores with a response time of about 15 minutes or less, a sensitivity of $10^5$ spores/ml, and a dynamic range of four orders of magnitude. The sensitivity can be improved by optimizing aerosol collection and spectrometer performance. Ultimately, the most attractive feature we have demonstrated is the unattended monitoring of aerosolized bacterial spores for the duration of a workday (i.e. ~8 hrs).

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

In summary, methods and apparatus for assays of bacterial spores have been described. A sample of unknown bacterial spores is added to a test strip. The sample of unknown bacterial spores is drawn to a first sample region on the test strip by capillary action. Species-specific antibodies are bound to the sample when the unknown bacterial spores match the species-specific antibodies, otherwise the sample is left unbound. DPA is released from the bacterial spores in the bound sample. The terbium ions are combined with the DPA to form a Tb-DPA complex. The combined terbium ions and DPA are excited to generate a luminescence characteristic of the combined terbium ions and DPA to detect the bacterial spores. A live/dead assay is performed by a release of the DPA for live spores and a release of DPA for all spores. The detection concentrations are compared to determine the fraction of live spores. Lifetime-gated measurements of bacterial spores to eliminate any fluorescence background from organic chromophores comprise labeling the bacterial spore contents with a long-lifetime lumophore and detecting the luminescence after a waiting period. Unattended monitoring of bacterial spores in the air comprises the steps of collecting bacterial spores carried in the air and repeatedly performing the Tb-DPA detection steps above. The invention is also apparatus for performing the various methods disclosed above.

We claim:

1. A method for detection of bacterial spores in air comprising:
   continuously and automatically collecting an air sample at predetermined time intervals;
   suspending the collected air sample corresponding to a respective time interval in a solution including lanthanide ions to form a suspended sample;
   treating the suspended sample to induce any bacterial spores present in the suspended sample to release dipicolinic acid (DPA);
   inducing combination of the released DPA with the lanthanide ions in the suspended sample to form a lanthanide-DPA complex;
   exciting the lanthanide-DPA complex to generate a luminescence characteristic of the lanthanide-DPA complex; and
   detecting the luminescence characteristic of the lanthanide-DPA complex to determine the presence of any bacterial spores in the air sample.

2. The method of claim 1, wherein the continuously and automatically collecting the air sample comprises capturing the air sample with an aerosol sampler or impactor.

3. The method of claim 1, wherein the detecting the luminescence characteristic to determine the presence of any bacterial spores comprises monitoring the luminescence characteristic.

4. The method of claim 1, wherein the continuously and automatically collecting the air sample comprises automatically collecting a new air sample four times every hour.

5. The method of claim 1, wherein the detecting the luminescence characteristic to determine the presence of any bacterial spores comprises continuously monitoring the luminescence characteristic.

6. The method of claim 1, wherein the treating the suspended sample comprises microwaving the suspended sample to heat the solution suspended sample and form a heated sample solution.

7. The method of claim 1, wherein the treating the suspended sample comprises heating the suspended sample to form a heated sample solution, and the inducing combination of the released DPA with the lanthanide ions comprises cooling the heated sample solution to increase formation of the lanthanide-DPA complex.

8. The method of claim 1, further comprising generating an alarm signal when presence of bacterial spores is detected.

9. The method of claim 1, further comprising generating an alarm signal when a concentration of detected bacterial spores reaches a threshold concentration.

10. The method of claim 1, wherein the lanthanide ions comprise terbium ions.

11. The method of claim 1, wherein the treating the suspended sample comprises microwaving and/or sonicating the suspended sample.

12. The method of claim 6, wherein the inducing the combination of the released DPA with the lanthanide ions comprises cooling the heated sample solution to increase formation of the lanthanide-DPA complex.

13. The method of claim 1, wherein the detecting the luminescence characteristic of the lanthanide-DPA complex comprises detecting a luminescence intensity to quantify any bacterial spores in the sample.

14. The method of claim 13, wherein the detecting the luminescence characteristic of the lanthanide-DPA complex comprises continuously monitoring the luminescence intensity.

15. The method of claim 14, further comprising generating an alarm signal when presence of bacterial spores is detected.

16. The method of claim 14, further comprising generating an alarm signal when a concentration of detected bacterial spores reaches a threshold concentration.

* * * * *

UNITED STATES PATENT AND TRADEMARK OFFICE
CERTIFICATE OF CORRECTION

PATENT NO. : 10,612,067 B2
APPLICATION NO. : 15/666512
DATED : April 7, 2020
INVENTOR(S) : Adrian Ponce et al.

It is certified that error appears in the above-identified patent and that said Letters Patent is hereby corrected as shown below:

In the Claims
Column 14, Line 54, Claim 6    after "to heat the" delete "solution"

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*